US008425883B2

(12) United States Patent
Golz-Berner et al.

(10) Patent No.: US 8,425,883 B2
(45) Date of Patent: Apr. 23, 2013

(54) COSMETIC SUN PROTECTION PRODUCT BASED ON W/SI-EMULSIONS

(75) Inventors: Karin Golz-Berner, Monaco (MC); Leonhard Zastrow, Monaco (MC); Melle Sandra Miton, Nice (FR)

(73) Assignee: Coty Prestige Lancaster Group GmbH, Mainz (DE)

( * ) Notice: Subject to any disclaimer, the term of this patent is extended or adjusted under 35 U.S.C. 154(b) by 687 days.

(21) Appl. No.: 12/280,185

(22) PCT Filed: Feb. 20, 2007

(86) PCT No.: PCT/EP2007/051608
§ 371 (c)(1),
(2), (4) Date: Nov. 7, 2008

(87) PCT Pub. No.: WO2007/096353
PCT Pub. Date: Aug. 30, 2007

(65) Prior Publication Data
US 2009/0185989 A1    Jul. 23, 2009

(30) Foreign Application Priority Data
Feb. 21, 2006 (DE) .......................... 10 2006 008 920

(51) Int. Cl.
*A61K 8/06* (2006.01)
*A61Q 17/04* (2006.01)
(52) U.S. Cl.
USPC .......................................................... 424/59
(58) Field of Classification Search .................. None
See application file for complete search history.

(56) References Cited

U.S. PATENT DOCUMENTS

| 5,232,688 | A | * | 8/1993 | Ziegler et al. | 424/59 |
| 5,783,174 | A | * | 7/1998 | Deckner | 424/59 |
| 6,274,151 | B1 | * | 8/2001 | Michel et al. | 424/401 |
| 6,667,046 | B2 | * | 12/2003 | Leo et al. | 424/401 |
| 2002/0022040 | A1 | * | 2/2002 | Robinson et al. | 424/401 |
| 2005/0063925 | A1 | * | 3/2005 | Candau et al. | 424/59 |

FOREIGN PATENT DOCUMENTS

| CA | 2 138 974 | | 1/1994 |
| FR | 2883172 A1 | * | 9/2006 |
| WO | 2005039520 A1 | | 4/2005 |
| WO | 2005/103659 | | 11/2005 |
| WO | 2006110271 A1 | | 10/2006 |

* cited by examiner

*Primary Examiner* — James H. Altrum-Acevedo
*Assistant Examiner* — Jessica Kassa
(74) *Attorney, Agent, or Firm* — Novak Druce Connolly Bove + Quigg LLP

(57) ABSTRACT

The invention relates to a cosmetic sun protection product based on W/Si emulsions, which product has improved effectiveness and, despite high content of organic sun protection filters, a very good sensory profile and, in particular, a long-lasting soft touch. The sun protection product includes 22-32 wt. % of a volatile, cyclic silicone oil, 2.0-4.0 wt. % of a non-volatile silicone elastomer, 0.9-2.8 wt. % of an emulsifier, 0.1-0.5 wt. % of an amino acid/fatty acid copolymer, 19-24 wt. % of a mixture of organic UVA and UVB filters at a ratio of from 1:1.5 to 1:1; and cosmetic adjuvants, excipients, active substances and mixtures thereof to make 100 wt. %, the Brookfield viscosity of the sun protection product ranging from 3,000 to 20,000 mPas.

1 Claim, No Drawings

COSMETIC SUN PROTECTION PRODUCT BASED ON W/SI-EMULSIONS

CROSS-REFERENCE TO RELATED APPLICATIONS

This application is a §371 national stage of PCT/EP2007/051608, filed Feb. 20, 2007, which claims priority to German Patent Application No. 10 2006 008 920.0, filed Feb. 21, 2006, both of which are hereby incorporated by reference.

The invention relates to a cosmetic sun protection product based on W/Si emulsions, which product has improved effectiveness.

Apart from some advantages, including organic sun protection filters in modern skin care products based on silicone oil has a number of drawbacks. Sun protection preparations having high sun protection factors (SPF>15) require incorporation of significantly higher amounts of organic sun protection filters than would be theoretically required to achieve an appropriate SPF because silicone oils do not readily take up such filters and exhibit a property which reduces the SPF. Furthermore, satisfactory texture of the emulsion is difficult to achieve with increasing concentrations of filters. The soothing touch is lost, whitening effects appear, and the softness during and after applying the product to the skin becomes unsatisfactory.

DE 102 34 884 A1 describes a multi-phase cosmetic sunscreen preparation which, being an Si/N emulsion, includes more than 50% silicone oil in the fatty phase, as well as polyether-modified polysiloxanes and UV filters, and wherein at least one of the two, three or four phases is non-transparent or non-translucent. The invention does not aim for such a multi-phase character.

The invention is based on the object of developing a cosmetic sun protection product on the basis of W/Si emulsions, which product, despite high content of organic sun protection filters, has a very good sensory profile and, in particular, a long-lasting soft touch.

According to the invention, the sun protection product on the basis of W/Si emulsions comprises
22-32 wt. % of a volatile, cyclic silicone oil with a heat of vaporization in the range of from 150 to 180 kJ/kg;
2.0-4.0 wt. % of a non-volatile silicone elastomer or a mixture of a plurality of non-volatile silicone elastomers;
0.9-2.8 wt. % of an emulsifier or a mixture of emulsifiers;
0.1-0.5 wt. % of an amino acid/fatty acid copolymer;
19-24 wt. % of a mixture of organic UVA and UVB filters at a ratio of from 1:1.5 to 1:1;
and cosmetic adjuvants, excipients, active substances and mixtures thereof to make 100 wt. %, all data being based on the overall weight of the sun protection product,
and the Brookfield viscosity of the sun protection product ranging from 3,000 to 20,000 mPas.

In a particularly preferred fashion the formulation does not additionally include vegetable, animal or mineral oils.

In a likewise preferred fashion the non-volatile silicone elastomers are substances selected from the group consisting of crosslinked polysiloxanes, high-molecular weight silicone polyethers, copolymers of polydimethylsiloxane and dimyldimethylsiloxane and mixtures thereof.

In a likewise preferred fashion the emulsifier is a mixture of emulsifiers, e.g. a mixture of anionic and non-ionic emulsifiers, preferably selected from the group consisting of fatty alcohol salts, fatty ether salts, fatty acid esters and mixtures thereof. More specifically, the fatty alcohol is a behenyl alcohol. Particularly preferred fatty acid esters are e.g. glyceryl stearate or glyceryl stearate citrate. A preferred fatty alcohol salt is sodium lauryl ether sulfate or sodium dicocoylethylenediamine-PEG-15 sulfate. An emulsifying mixture of the above-mentioned substances achieves advantageous fixing of the system components and, as a consequence, exceptional stability of the cosmetic formula.

When judging the sensory properties of the sun protection product according to the invention, especially those such as whitening effect on the skin upon spreading, gliding of the cream body between the fingers (texture), film thickness upon spreading (spreading effect), duration of spreading effect, tackiness after spreading, softness after spreading, fatty touch after spreading, gloss after spreading, powdery touch after spreading and general skin comfort must be taken into account.

The sun protection product of the invention was found to be excellent in most of these sensory properties. More specifically, the texture, general skin comfort and soft touch after spreading on the skin and during a long period thereafter are improved compared to other products.

Furthermore, the excellent spreading on skin of the organic sun protection filters within the system of the invention as well as its homogeneity on the skin are particularly noteworthy.

Another feature of the invention is the viscosity which preferably ranges from 4,000 to 15,000 mPas. The viscosity is measured at 20° C. using a Brookfield DV-II+ viscometer (Brookfield Engin. Lab., Inc., Stroughton, Mass., USA), 3,000 to 10,000 mPas disc spindle, and >10,000 to 20,000 Helipath TC/TD spindle.

Furthermore, the product according to the invention includes cosmetic adjuvants and excipients as commonly used in such preparations, e.g. water, preservatives, dyes, pigments having a coloring effect, thickening agents, odorous substances, alcohols, polyols, oils, esters, electrolytes, gel-forming agents, polymers, copolymers, emulsifiers, silicone waxes and stabilizers.

Pigments, pigment mixtures or powders with a pigment-like effect, also including those with a pearl-gloss effect, may comprise, for example, iron oxides, natural aluminum silicates such as ochre, titanium oxide, mica, kaolin, manganese-containing clays, calcium carbonate, talc, mica-titanium oxide, mica-titanium oxide-iron oxide, bismuth oxychloride, nylon beads, ceramic beads, expanded and non-expanded synthetic polymer powders, powdery natural organic compounds such as milled solid algae, milled plant parts.

Suitable gel-forming agents include carbomer, xanthan gum, carrageenan, acacia gum, guar gum, agar, alginates and tyloses, carboxymethylcellulose, hydroxyethylcellulose, quaternized cellulose, quaternized guar, specific polyacrylates, polyvinyl alcohol, polyvinylpyrrolidone, montmorillonite.

Likewise, polyols are possible components of the product according to the invention. For example, said polyols are propylene glycol, dipropylene glycol, ethylene glycol, isoprene glycol, glycerol, butylene glycol, sorbitol and mixtures thereof. The share of polyol is in the range of from 0.1 to 40 wt. %, preferably from about 5 to about 20 wt. % of the gel composition.

According to the invention, the sun protection product includes appropriate water- and/or oil-soluble UVA and UVB filters. Advantageous oil-soluble UVB filters include 4-aminobenzoic acid derivatives such as 2-ethylhexyl 4-dimethylamino-benzoate; esters of cinnamic acid such as 2-ethylhexyl 4-methoxycinnamate; benzophenone derivatives such as 2-hydroxy-4-methoxybenzophenone; benzo-phenone derivatives such as 2-hydroxy-4-methoxybenzophenone; 3-benzylidenecamphor derivatives such as 3-benzylidenecamphor.

Preferred oil-soluble UV filters are benzophenone-3, butyl-methoxybenzoyl-methane, octyl methoxycinnamate, octyl salicylate, 4-methylbenzylidencamphor, homosalates and octyl dimethyl PABA.

Water-soluble UVB filters are e.g. sulfonic acid derivatives of benzophenone or of 3-benzylidenecamphor or salts such as the Na or K salt of 3-phenyl-benzimidazole-5-sulfonic acid.

UVA filters include dibenzoylmethane derivatives such as 1-phenyl-4-(4'-isopropylphenyl)propane-1,3-dione, butylmethoxybenzoylmethane and menthyl anthranilate.

Particularly preferred are benzophenone-3, butylmethoxydibenzoylmethane, octyl methoxycinnamate, octyl salicylate, 4-methylbenzylidenecamphor, homosalates, octocrylene, ethylhexyl methoxycinnamate, isoamyl p-methoxycinnamate, octyl dimethyl PABA, ethylhexyltriazone, diethylhexylbutamidotriazone, ethylhexyl salicylate, methylene-bis(benzotriazolyl)tetramethylbutylphenol, disodium phenyldibenzimidazoletetrasulfonate, bis-ethylhexyloxyphenol methoxy-phenyltriazine and mixtures thereof.

Furthermore, broad-spectrum filters such as bis-resorcinyltriazine derivatives, but also benzoxazoles or UV Pearls® (Merck, Germany), can be used, the latter being constituted of water, ethylhexyl methoxycinnamate, silica, PVP, ethanol, sodium citrate, chlorophenesine, cetrimonium chloride.

The sun protection factor, SPF, is usually determined according to the COLIPA method (Colipa Ref.: 94/289 (1994)), which method essentially detects UVB radiation only. The in vivo UVA protection factors are determined using the persistent pigment darkening (PPD) as the end point (Photodermatol. Photoimmunol. Photomed. 16, 245-249 (2000)).

The method described in WO 2005/103659 is the very first to take into account that the origin of any skin damage related to the action of total UV is the total number of free radicals produced. This number depends on the overall UV dose rather than the intensity of UV rays. The total number of free radicals produced can be precisely measured by means of ESR, and an integrated SPF can be determined which provides the user with exact information on the actual degree of protection from UV radiation.

Such an SPF is integrated in two senses: it encompasses the entire UV spectrum as well as the complete depth up to which the skin can be damaged by UV radiation.

Another advantage in measuring the integrated SPF, or ISPF, is achieved in that measurement can be effected with the same or even increased reliability using 2 to 4 pieces of skin having 1 cm² each and obtained from human skin surgery or skin substrates (artificial skin), or directly on pig skin, instead of measuring the appearance of an erythema on the skin of a test person after conducting an ethically questionable treatment with radiation. In this way, there will be no radiation damage to the skin of test persons because this measuring method does not require test persons per se. According to the COLIPA standard, 10-20 volunteers are needed. In addition, the consequences of long waiting times before receiving the results are avoided, and there is no need to define certain standards which are required as a reference for evaluation in the known methods.

Determination of the ISPF considerably reduces costs both from an equipment and a methodological point of view since, already at present, an RGV measurement involves only half to one third of the costs of traditional methods of SPF determination.

In addition, the ISPF can be measured and calculated with an accuracy of about ±10%, while the accuracy of the traditional SPF measuring method, i.e., COLIPA (UVB protection), is only ±20-25%, or even 30-50% for high SPFs measured in different testing institutes.

The ISPF of the sun protection products according to the invention is in the range of 12-25. One particular advantage is that the share of UVA filters is in the range of the UVB filters, especially at a UVA filter/UVB filter ratio in the range of from 1:1.5 to 1:1.

Cosmetic active substances which can be additionally present in the product according to the invention include e.g. self-tanning agents such as those based on dihydroxyacetone, whitenings, free-radical scavengers, moisturizers, vitamins, enzymes, vegetable active substances, polymers, antioxidants, antiphlogistic natural active substances, oxygen-loaded asymmetric lamellar aggregates according to WO 94/00109, digestion products of yeasts or plant materials obtained using a mild ultrasonic digestion process according to WO 94/13783, kaolin as well as $SiO_2$-modified kaolin according to WO 94/17588.

Additionally included antioxidants and free radical-scavengers include vitamins such as vitamin C and derivatives thereof, e.g. ascorbyl acetates, phosphates and palmitates; vitamin A and derivatives thereof; folic acid and its derivatives, vitamin E and its derivatives such as tocopheryl acetate; flavones or flavonoids; amino acids such as histidine, glycine, tyrosine, tryptophan and derivatives thereof; carotenoids and carotenes such as α-carotene, β-carotene; uric acid and derivatives thereof; α-hydroxy acids such as citric acid, lactic acid, malic acid; stilbenes and derivatives thereof.

Common moisturizers are, for example, glycerol, butylene glycol, propylene glycol and mixtures thereof.

Whitenings for skin and hair are e.g. ursolic acid, Agouti peptides, glycyrrhiza root extract, hydroquinone, green tea extract, arbutin, biotin, mulberry extract (*Uvae ursii*), glycyrrhizine, placenta extract, ascorbyl glucosides, endothelin antagonists from chamomile extract.

The cosmetic preparation according to the invention can be used e.g. in sun creams, sun gels, after-sun products, day creams, night creams, masks, body lotions, makeups, lipsticks, eye cosmetics, hair masks, hair conditioners, shampoos, shower gels, shower oils, bathing oils. Such products are manufactured in a way well-known to those skilled in the art.

With reference to the examples, the invention will be illustrated in more detail below. All data are given in percent by weight, unless otherwise stated. Ambient temperature means 18-25° C.

EXAMPLE 1

W/Si Sun Emulsion SPF 60 (ISPF 20)

| | |
|---|---|
| (1) Cyclopentasiloxane & PEG-12 dimethicone crosspolymer (DC 9011) | 16 |
| (2) Cyclopentasiloxane & PEG/PPG-18/18 dimethicone & cyclotetrasiloxane (DC5225) | 4 |

-continued

| | |
|---|---|
| (3) Cyclopentasiloxane & cyclotetrasiloxane (DC 245) | 10 |
| (4) Deionized water | q.s. ad 100 |
| (5) Divinyldimethicone/dimethicone copolymer & C12-13 Pareth-3 & C12-13 Pareth 23 & cyclotetrasiloxane (HMW 2220) | 1 |
| (6) Methylene-bisbenzotriazolyl & tetramethylbutylphenol (Tinosorb M) | 6 |
| (7) Sodium laureth sulfate | 1.5 |
| (8) Sodium chloride | 1.2 |
| (9) Butyl-methoxydibenzoylmethane | 2 |
| (10) Bis-ethylhexyloxyphenol methoxyphenyltriazine | 2 |
| (11) Ethylhexyltriazone | 2 |
| (12) Isoamyl p-methoxycinnamate | 10 |
| (13) Preservative | 0.6 |
| (14) Palmitoylproline & palmitic acid & magnesium palmitoylglutamate & sodium palmitoylsarcosinate | 0.3 |
| (15) Behenyl alcohol & glyceryl stearate & glyceryl stearate citrate & sodium dicocoylethylenediamine PEG-15 sulfate | 0.3 |
| (16) Alcohol | 4 |
| (17) Perfume | 0.2 |

The silicon oil-containing components are mixed at ambient temperature, and the oil-soluble sun protection filters are added. Separately, water is mixed with the water-soluble components. Thereafter, the two phases are mixed at ambient temperature and homogenized. Viscosity: 5,170 mPas.

EXAMPLE 2

W/Si Sun Emulsion SPF 50 (ISPF 15)

A similar formulation as in Example 1 was produced, with the following differences:
(1) 15%; (7) 1.5%; (8) 0.8%; (11) and (15) 0% each.
The production procedure corresponded to that of Example 1.
Viscosity: 8,530 mPas.

EXAMPLE 3

W/Si Sun Emulsion SPF 50 (ISPF 12)

A similar formulation as in Example 1 was produced, with the following differences:
(1) 18%; (2) 3%; (7) 1%; (8) 0.8%; (10) 1%; (16) 4%.
The production procedure corresponded to that of Example 1.
Viscosity: 6,320 mPas.

EXAMPLE 4

Sensory Test

Part A
The following data were collected from a group of subjects including 2×9 subjects, each one testing the products of Example 1 and a comparative product according to the following evaluation criteria and giving a score between 1 and 9. The values quoted are mean values of all 18 subjects.
Product of Example 1 (Invention): A
Comparative product: B
The comparative product B consisted of 50% volatile silicone oil, 5% cyclodimethicone copolymer, 2% of the amino acid derivative Amisoft CA, 0.5% sodium stearate emulsifier, 8% UVA filters, 14% UVB filters, water, preservatives, perfume.
1. Whitening effect upon spreading on the skin:
   A=2.4 B=4.8
   Invention superior by 1.8 points
2. Gliding of cream body between the fingers (texture):
   A=8.2 B=3.4
   Invention superior by 4.8 points
3. Film thickness upon spreading:
   A=4.1 B=2.9
   Invention superior by 1.2 points and thus more homogeneous
4. Time up to final distribution (playtime):
   A=2.2 B=4.2
   Invention superior by 2.0 points
5. Tackiness after spreading:
   A=2.6 B=2.7
   Both virtually identical
6. Fatty touch after spreading:
   A=4.0 B=4.8
   Invention superior by 0.8 points
7. Gloss after spreading:
   A=2.1 B=2.0
   Both virtually identical
8. Softness of skin after spreading:
   A=6.8 B=5.3
   Invention superior by 1.5 points
9. Powdery touch after spreading:
   A=3.8 B=2.4
   Invention superior by 1.4 points
10. General skin comfort (evaluation 3, 5, 7, 8, 9, 10)
    A=+4.1 B=0
    Invention superior by 4.1 points As can be seen from the above, 8 properties were given higher scores and 2 properties were rated virtually identical. Consequently, the product according to the invention can be rated as significantly better in its sensory properties than a comparable product.

Part B
For the test relating to the softness of the skin following application, the subjects (groups A and B) were questioned in the following chronological order. The numbers following the group letters represent the number of subjects relating to the corresponding remark.

| | REMARK | | |
|---|---|---|---|
| TIME | Very soft | Soft | Moderately soft |
| Immediately after application | A7 B5 | A2 B4 | A0 — |
| 30 min after | A6 B5 | A3 B3 | A0 B1 |
| 2 h after | A6 B4 | A2 B2 | A1 B2 |

-continued

| TIME | REMARK | | |
|---|---|---|---|
| | Very soft | Soft | Moderately soft |
| 4 h after | A4 B2 | A3 B3 | A2 B4 |
| 8 h after | A4 B0 | A2 B2 | A3 B7 |

While 4 and 2 subjects from group A after 8 hours still rated the soft touch "very soft" and "soft", respectively, it was only 2 subjects in group B who rated "soft", thereby clearly demonstrating the long-lasting effectiveness of the product according to the invention.

The invention claimed is:

1. A sun protection product on the basis of W/Si emulsion, comprising:
   16% by weight a mixture of cyclopentasiloxane and PEG-12 dimethicone crosspolymer;
   4% by weight a mixture of cyclopentasiloxane and PEG/PPG-18/18 dimethicone and cyclotetrasiloxane;
   10% by weight a mixture of cyclopentasiloxane and cyclotetrasiloxane;
   1% by weight a mixture of divinyldimethicone/dimethicone copolymer and $C_{12\text{-}13}$ Pareth-3 and $C_{12\text{-}13}$ Pareth 23 and cyclotetrasiloxane;
   6% by weight a mixture of methylene-bisbenzotriazolyl and tetramethylbutylphenol;
   1.5% by weight sodium laureth sulfate;
   1.2% by weight sodium chloride;
   2% by weight butyl-methoxydibenzoylmethane;
   2% by weight bis-ethylhexyloxyphenol methoxyphenyltriazine;
   2% by weight ethylhexyltriazone;
   10% by weight isoamyl p-methoxycinnamate;
   0.6% by weight preservative;
   0.3% by weight a mixture of palmitoylproline and palmitic acid and magnesium palmitoylglutamate and sodium palmitoylsarcosinate;
   0.3% by weight a mixture of behenyl alcohol and glyceryl stearate and glyceryl stearate citrate and sodium dicocoylethylenediamine PEG-15 sulfate;
   4% by weight alcohol;
   0.2% by weight perfume;
   and q.s. ad 100% by weight deionized water,
   wherein all weight percentages are based on the overall weight of the sun protection product, and the Brookfield viscosity of the sun protection product ranging from 3,000 to 20,000 mPas.

* * * * *